United States Patent [19]
Inoue et al.

[11] 3,950,325
[45] Apr. 13, 1976

[54] NOVEL PROCESS FOR PREPARING 2,2'-CYCLOCYTIDINE OR 1-β-D-ARABINOFURANOSYL CYTOSINE

[75] Inventors: Ichizo Inoue, Ikeda; Takeshi Adachi, Nishinomiya; Kazuhiko Kondo, Osaka, all of Japan

[73] Assignee: Tanabe Seiyaku Co., Ltd., Osaka, Japan

[22] Filed: Jan. 21, 1975

[21] Appl. No.: 542,817

[30] Foreign Application Priority Data
Jan. 30, 1974 Japan.............................. 49-13118

[52] U.S. Cl........................................... 260/211.5 R
[51] Int. Cl.²....................................... C07H 17/02
[58] Field of Search............................ 260/211.5 R

[56] References Cited
UNITED STATES PATENTS

| | | | |
|---|---|---|---|
| 3,322,747 | 5/1967 | Shen et al. | 260/211.5 R |
| 3,709,874 | 1/1973 | Moffatt et al. | 260/211.5 R |

*Primary Examiner*—Johnnie R. Brown
*Attorney, Agent, or Firm*—Jordan B. Bierman; Linda Bierman; Kenneth J. Stempler

[57] ABSTRACT 2,2'-Cyclocytidine is prepared by reacting cytidine with a functional derivative of silicon, and hydrolyzing the reaction product under acidic conditions. 1-β-D-Arabinofuranosyl cytosine is prepared by reaction of cytidine with a functional derivative of silicon, followed by alkaline hydrolysis of the reaction product. 2,2'-Cyclocytidine and 1-β-D-arabinofuranosyl cytosine are useful as antitumor and antiviral agents.

8 Claims, No Drawings

NOVEL PROCESS FOR PREPARING 2,2'-CYCLOCYTIDINE OR 1-β-D-ARABINOFURANOSYL CYTOSINE

This invention relates to a novel process for preparing 2,2'-cyclocytidine or 1-β-d-arabinofuranosyl cytosine.

2,2'-Cyclocytidine and 1-β-arabinofuranosyl cytosine are useful as antitumor and antiviral agents in test animals.

Several methods for preparing 2,2'-cyclocytidine or 1-β-D-arabinofuranosyl cytosine have been known up to now. For example, 2,2'-cyclocytidine is prepared by refluxing cytidine and partially hydrolyzed phosphorus oxychloride in ethyl acetate [*Chemical ) Pharmaceutical Bulletin* 18 (1970), pages 2569–2571]; or by reaction of cytidine with a Vilsmeier-Haack reagent [*Tetrahedron Letters* (1970), pages 867–870]. 1-β-D-Arabinofuranosyl cytosine is prepared by alkaline hydrolysis of 2,2'-cyclocytidine [*Tetrahedron Letters* (1970), pages 867–870]; by refluxing $N^4$-acetylcytidine and partially hydrolyzed phosphorus oxychloride in ethyl acetate to give $N^4$, 3', 5'-triacetylarabinofuranosyl cytosine, and hydrolyzing said cytosine derivative with ammonia [*Chem. Pharm. Bull.* 18 (1970), pages 2569–2571]; or by reaction of cytidine or $N^4$-acetylcytidine with acetyl bromide in acetonitrile to give 1-(2,5-diacetyl-3-bromo-3-deoxy-β-D-xylofuranosyl)-cytosine or $N^4$-acetyl derivative thereof, followed by hydrolysis with sodium hydroxide [Japanese Pat. No. 24399/1973]. Alternatively, 1-β-D-arabinofuranosyl cytosine is prepared by the steps of reacting cytidine with phosphoric acid, heating the resultant 2,2'-cyclocytidine-3',5'-O-polyphosphate under acidic conditions, and hydrolyzing the reaction product with lithium hydroxide to give arabinofuranosyl cytosine 3',5'-diphosphate, followed by dephosphorilation thereof with alkaline phosphatase. However, these known methods are still disadvantageous for commercial production of 2,2'-cyclocytidine or 1-β-D-arabinofuranosyl cytosine because of poor yield of the said products and/or troublesome reaction procedures employed therein.

As a result of investigations, we have found a novel and convenient method which enables the preparation of 2,2'-cyclocytidine or 1-β-D-arabinofuranosyl cytosine.

According to the present invention, 2,2'-cyclocytidine can be prepared by (1) reacting cytidine with a functional derivative of silicon, and (2) hydrolyzing the reaction product under acidic conditions. 1-β-D-Arabinofuranosyl cytosine can be prepared by (1) reacting cytidine with a functional derivative of silicon, and (3) hydrolyzing the reaction product under alkaline conditions. Alternatively, 1-β-D-arabinofuranosyl cytosine may be prepared by (4) alkaline hydrolysis of 2,2'-cyclocytidine obtained in the abovementioned Step (2).

These reactions are respectively shown by the following scheme:

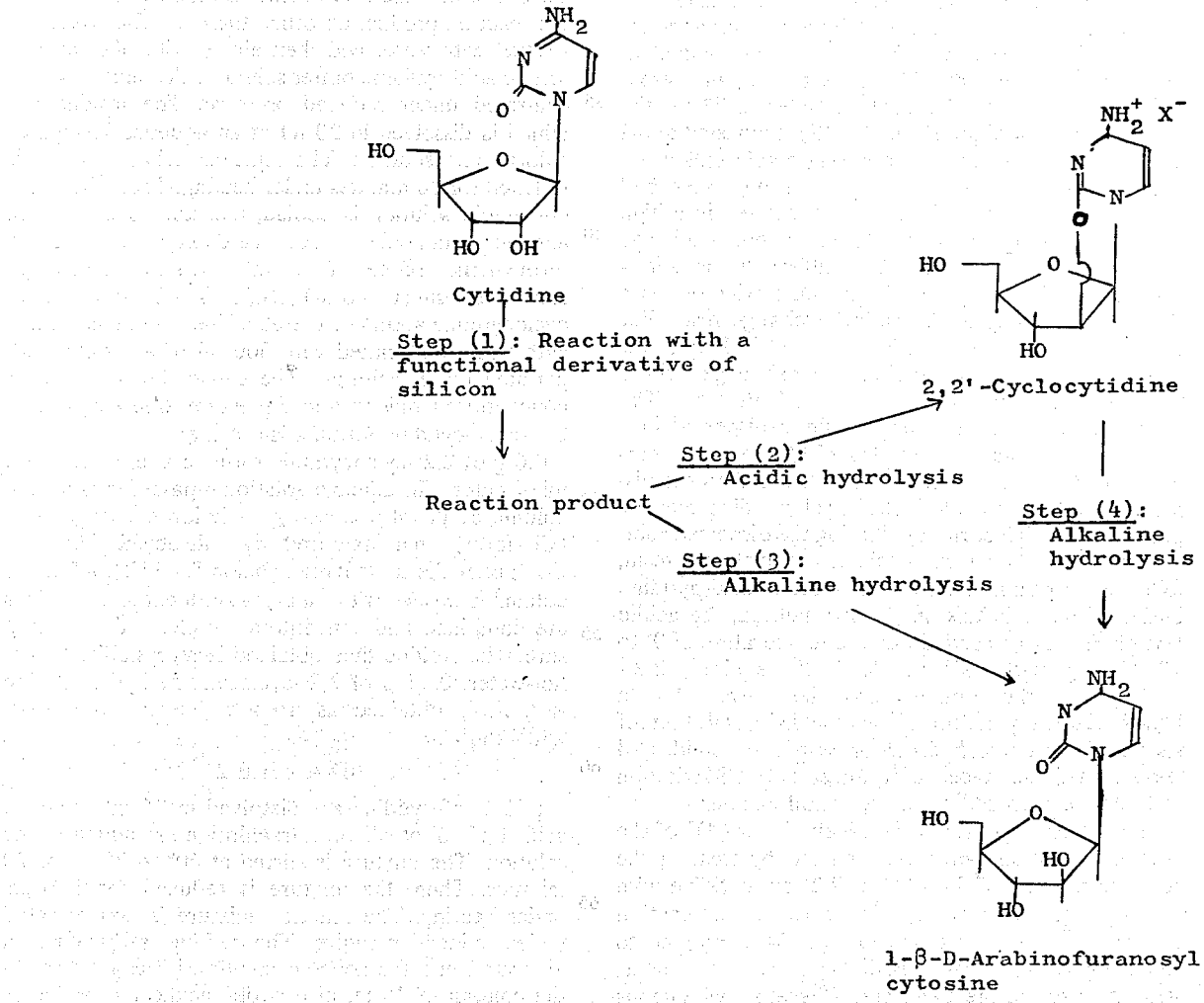

wherein X is an organic or inorganic acidic residue.

In the method of the present invention, various silicon compounds can be employed as the functional derivative of silicon. The functional derivative of silicon suitable for use in the present invention includes, for example, silicon tetrahalide (e.g., silicon tetrachloride, silicon tetrabromide), tetra-lower aliphatic acyloxy silane (e.g., silicon tetraacetate, silicon tetrapropionate) and silicon oxyhalide (e.g., silicon oxychloride).

The reaction of cytidine with the functional derivative of silicon [i.e., Step (1)] can be conducted at a temperature of 20° to 150°C in a solvent, if required, in the presence of a Lewis acid. The addition of the Lewis acid such as a mineral acid (e.g., hydrochloric acid, sulfuric acid) or boron trihalide (e.g., boron trifluoride) to the reaction solution is especially preferred to facilitate the reaction of cytidine and tetra-lower aliphatic acyloxy silane. The suitable amount of the Lewis acid to be added may be 0.1 to 20 moles, especially 1 to 5 moles (per mole of cytidine). Further, in carrying out the reaction, it is preferred to use 1.5 to 5 moles (per mole of cytidine) of the functional derivative of silicon. Acetic acid, propionic acid and the like are preferably employed as the reaction solvent.

The acidic hydrolysis [i.e., Step (2)] and the subsequent purification procedures are readily accomplished. For example, the reaction solution obtained in Step (1) is evaporated to remove solvent. The reaction product thus separated is hydrolyzed with a mineral acid such as hydrochloric acid or sulfuric acid in a solvent. Said hydrolysis is carried out at a temperature of 0° to 100°C, especially 10° to 40°C. Water and alkanols of one to five carbon atoms (e.g., methanol, ethanol) are suitable as the reaction solvent. Then, the reaction solution obtained in Step (2) is adjusted to pH 1 to 5 and contacted with a strong acidic cation exchange resin to have 2,2'-cyclocytidine adsorbed thereon. 2,2'-Cyclocytidine may be isolated in a high purity by eluting the strong acidic cation exchange resin with a formic acid-pyridine buffer solution. Alternatively, the acidic hydrolysis may be carried out with the aid of a strong acidic cation exchange resin. For example, the reaction solution obtained in Step (1) is contacted with a strong acidic cation exchange resin to have the reaction product adsorbed thereon. The strong acidic cation exchange resin is dispersed in a solvent such as water or an alkanol of one to five carbon atoms (e.g., methanol, ethanol), and then the dispersed solution is heated. 2,2'-Cyclocytidine may be obtained in a high purity by filtering the dispersed solution to collect the strong acidic cation exchange resin, followed by elution thereof with a formic acid-pyridine buffer solution. In this alternative method, the acidic hydrolysis may be carried out at a temperature of 0° to 100°C, especially 60° to 70°C. If required, 2,2'-cyclocytidine thus obtained may be converted to a pharmaceutically acceptable acid addition salt thereof such as, for example, hydrochloride, hydrobromide and lactate. Said pharmaceutically acceptable acid addition salt may be prepared by conventional manner.

The alkaline hydrolysis [i.e., Step (3) or (4)] of the present invention can be carried out by treating the reaction product of Step (1) or 2,2'-cycloctidine with an alkali agent in a solvent. For example, the reaction solution obtained in Step (1) or (2) is evaporated to remove solvent, and the residue is dissolved in water. After addition of the alkali agent thereto, the aqueous solution is stirred until the hydrolysis is completed. It is preferred to carry out the alkali hydrolysis at a pH of 12 to 14. It is also preferred to carry it out at a temperature of 0° to 50°C. Potassium hydroxide, potassium carbonate, sodium carbonate, lithium hydroxide, lithium carbonate and sodium hydroxide are suitably employed as the alkali agent. 1-β-D-Arabinofuranosyl cytosine produced in the abovementioned step may be easily isolated and purified by conventional manner, for example, by chromatography on a column of an ion exchange resin.

Practical and presently-preferred embodiments of the present invention are illustratively shown in the following Examples:

In this specification and claims, the term "lower aliphatic acyloxy" should be interpreted as referring to an aliphatic acyloxy group having one to four carbon atoms.

EXAMPLE 1

1.25 G of cytidine are dissolved in 25 ml of acetic acid. 1.19 ml of silicon tetrachloride are added to the solution. The mixture is stirred at 60° to 70°C for 20 minutes. Then, the mixture is refluxed for 3 hours under heating. The reaction mixture is concentrated under reduced pressure. The residue is dissolved in ice-water, and the aqueous solution is passed through the column of 25 ml of a strong acidic ion exchange resin ($H^+$-form) (manufactured by Mitsubishi Chemical Co., under the trade name: Diaion SK-IB) to have the reaction product adsorbed thereon. The column is washed with water and then eluted with 300 ml of a formic acid-pyridine buffer solution. The eluate is concentrated under reduced pressure. The residue obtained is dissolved in 20 ml of an aqueous 1N-hydrochloric acid solution. The aqueous acidic solution is refluxed for 30 minutes under heating. Then, the aqueous acidic solution is cooled, adjusted to pH 2 with aqueous ammonia under ice-cooling and passed through the column of 25 ml of a strong acidic ion exchange resin ($H^+$-form) (Diaion SK-IB) to have 2,2'-cyclocytidine adsorbed thereon. The column is washed with water and eluted with 300 ml of a formic acid-pyridine buffer solution. The eluate thus obtained is concentrated under reduced pressure, whereby 0.6 g of 2,2'-cyclocytidine formate is obtained.

0.6 g of 2,2'-cyclocytidine formate is dissolved in 3 ml of water. The aqueous solution is passed through the column of 11 ml of a strong basic ion exchange resin ($Cl^-$-form) (manufactured by Mitsubishi Chemical Co., under the trade name: Diaion SA-11B). After the column is washed with water, the effluent and washings are combined and concentrated under reduced pressure. The residue thus obtained is recrystallized from hot-water. 0.45 G of 2,2'-cyclocytidine hydrochloride is thereby obtained as needles. Yield: 34 % M.p. 258°–260°C.

EXAMPLE 2

1.25 G of cytidine are dissolved in 25 ml of acetic acid. 1.19 ml of silicon tetrachloride are added to the solution. The mixture is stirred at 60° to 70°C for 20 minutes. Then, the mixture is refluxed for 3 hours under heating. The reaction mixture is concentrated under reduced pressure. The residue is dissolved in ice-water, and the aqueous solution is passed through the column of 25 ml of a strong acidic ion exchange resin (H$^+$-form) (Diaion SK-IB) to have the reaction product adsorbed thereon. The strong acidic ion exchange resin is washed with water and dispersed into 30 ml of methanol. The dispersed solution is refluxed for 30 minutes under heating. Then, the dispersed solution is filtered to collect insoluble materials. The strong acidic ion exchange resin thus collected is charged into a column. After washed with water, the column is eluted with 750 ml of a formic acid-pyridine buffer solution. The eluate thus obtained is concentrated under reduced pressure, and the residue is washed with methanol. 1.0 g of 2,2'-cyclocytidine formate is thereby obtained.

1.0 g of 2,2'-cyclocytidine formate is treated in the same manner as described in Example 1. 0.7 g of 2,2'-cyclocytidine hydrochloride is obtained as colorless needles. Yield: 52 % M.p. 258°–260°C (decomp.) (recrystallized from hot-water)

EXAMPLE 3

5 G of cytidine are dissolved in 50 ml of acetic acid. 4.75 ml of silicon tetrachloride are added to the solution. The mixture is stirred at 60° to 70°C for 20 minutes. Then, the mixture is refluxed for 3 hours under heating. The reaction mixture is concentrated under reduced pressure. The residue is dissolved in ice-water, and the aqueous solution is adjusted to pH 12.5 with an aqueous 2 N-sodium hydroxide solution. After the aqueous solution is stirred at room temperature for 30 minutes, said solution is passed through a column of 200 ml of a strong acidic ion exchange resin (H$^+$-form) (Diaion SK-IB). The column is washed with water and eluted with 1300 ml of aqueous 1N-ammonia. The eluate is concentrated under reduced pressure. The residue thus obtained is crystallized with ethanol and then recrystallized from 50 % ethanol. 2.7 G of 1-β-D-arabinofuranosyl cytosine are thereby obtained. Yield: 55 % M.p. 213°–214°C (decomp.)

EXAMPLE 4

1.0 G of cytidine is dissolved in 20 ml of acetic acid under heating. After cooling, 2.17 g of silicon tetraacetate are added to the solution. The mixture is stirred at 120°C for 5 minutes. The mixture is cooled to room temperature, and 0.6 ml of boron trifluoride-ether complex is added thereto. Then, the mixture is stirred at room temperature for 4 days. After the reaction, the mixture is concentrated under reduced pressure, and the residue is treated in the same manner as described in Example 3. 0.5 g of 1-β-D-arabinofuranosyl cytosine is thereby obtained. Yield: 50 % M.p. 213°–214°C (decomp.) (recrystallized from 50 % ethanol)

What we claim is:

1. A process for preparing 2,2'-cyclocytidine which comprises reacting cytidine with a silicon derivative taken from the class consisting of silicon tetrahalide, tetra lower-aliphatic acyloxy silicon, and silicon oxyhalide, and hydrolyzing the reaction product under acidic conditions.

2. The process according to claim 1, wherein the reaction of cytidine with the functional derivative of silicon is carried out at a temperature of 20° to 150°C in a solvent, and the subsequent hydrolysis is carried out by treating the reaction product with a mineral acid or a strong cation exchange resin at a temperature of 0° to 100°C in a solvent.

3. The process according to claim 1, wherein cytidine is reacted with 1.5 to 5 moles (per mole of cytidine) of the silicon derivative in the presence of 0.1 to 20 moles (per mole of cytidine) of a Lewis acid, and the subsequent hydrolysis is carried out by the use of a mineral acid or a strong cation exchange resin.

4. The process according to claim 3 wherein the hydrolysis is carried out at 0°–100°C. in a solvent.

5. A process for preparing 1-β-D-arabinofuranosyl cytosine which comprises reacting cytidine with a silicon derivative taken from the class consisting of silicon tetrahalide, tetra lower-aliphatic acyloxy silicon, and silicon oxyhalide, and hydrolyzing the reaction product under alkaline conditions.

6. The process according to claim 5 wherein the reaction is carried out at 20°–150°C. in a solvent, and the hydrolysis is carried out at 0°–50°C. under alkaline conditions in a solvent.

7. The process according to claim 2 wherein the hydrolysis is carried out at 60°–70°C.

8. The process according to claim 6, wherein cytidine is reacted with 1.5 to 5 moles (per mole of cytidine) of the functional derivative of silicon at a temperature of 20° to 150°C in the presence of 0.1 to 20 moles (per mole of cytidine) of a Lewis acid in a solvent, and the subsequent hydrolysis is carried out by treating the reaction product with an alkaline agent at a pH of 12 to 14 at a temperature of 0° to 50°C in a solvent.

* * * * *